United States Patent [19]

Hanby

[11] Patent Number: 4,992,379

[45] Date of Patent: Feb. 12, 1991

[54] FIELD TEST FOR AROMATICS IN GROUNDWATER

[76] Inventor: John D. Hanby, 2718 Meyer Rd., Seabrook, Tex. 77586

[21] Appl. No.: 933,020

[22] Filed: Feb. 5, 1987

[51] Int. Cl.$^5$ ............................................. G01N 33/22
[52] U.S. Cl. ........................................ 436/29; 210/691; 210/747; 436/25; 436/30; 436/31; 436/140
[58] Field of Search ................ 210/691, 747; 436/140, 436/25, 30, 31, 29

[56] References Cited

U.S. PATENT DOCUMENTS

| | | | |
|---|---|---|---|
| 2,398,580 | 4/1946 | Crawford | 436/30 |
| 2,854,396 | 9/1958 | Hunt et al. | 436/31 |
| 3,287,088 | 11/1966 | Seevers | 436/30 |
| 4,401,569 | 8/1983 | Thaveri et al. | 210/747 |
| 4,517,094 | 5/1985 | Beall | 210/694 |
| 4,549,966 | 10/1985 | Beall | 210/691 |
| 4,591,443 | 5/1986 | Brown et al. | 210/747 |
| 4,637,465 | 1/1987 | Gash | 210/747 |

OTHER PUBLICATIONS

Royston Roberts et al., "Modern Experimental Organic Chemistry", Saunders College HRW, pp. 176–182, 3rd Ed., 1979.

Royston Roberts et al., "Modern Experimental Organic Chemistry", Saunders College HRW, pp. 510–512, 3rd Ed., 1979.

Primary Examiner—Robert J. Warden
Assistant Examiner—Timothy M. McMahon
Attorney, Agent, or Firm—Sughrue, Mion, Zinn, Macpeak & Seas

[57] ABSTRACT

A simple, on-site, field test method and kit for aromatic contamination in a water sample is provided. In the field test, the water sample is first extracted using an alkyl halide extractant, with a Friedel-Crafts Lewis acid catalyst being added to the resulting extractant phase. A reaction product is thereby produced having a characteristic color indicative of the amount and type of aromatic contamination.

5 Claims, No Drawings

FIELD TEST FOR AROMATICS IN GROUNDWATER

BACKGROUND OF THE INVENTION

The present invention relates generally to field testing soil or groundwater for low-level contamination by organic (aromatic) chemicals. More particularly, the present invention relates to a test kit and method involving a Friedel-Crafts reaction for performing such field testing.

It has long been desired for a simple, accurate and efficient field test for determining the amount and type of aromatic contamination in soil and groundwater. No simple on-site field test for both qualitative and quantitative determination of aromatic contamination in a hydrous environment has proved effective.

The Friedel-Crafts alkylation reaction of an aromatic with an alkyl-halide in the presence of a metal-halide catalyst to introduce an alkyl group onto the aromatic is well known in the art. This well known Friedel-Crafts reaction has heretofore only been employed in completely anhydrous conditions. It has been surprisingly discovered, however, that a Friedel-Crafts reaction may be utilized in a simple on-site field test for both qualitative and quantitative determination of aromatic contamination in soil and groundwater.

SUMMARY OF THE INVENTION

In accordance with the present invention, there is provided a simple, on-site, field test kit and method for detecting both qualitatively and quantitatively aromatic contamination in soil and groundwater.

The method, in its overall concept, comprises the steps of first extracting a water sample containing the aromatic contamination with an alkyl halide extractant to produce an extractant phase and a water phase, separating the resulting extractant phase from the remaining water phase, then adding a Friedel-Crafts Lewis acid catalyst to this extractant phase. Adding the catalyst promotes the Friedel-Crafts reaction which in turn produces a reaction product having a characteristic color indicative of the aromatic contaminant(s). From this color, it can be determined both qualitatively what type, and quantitatively how much, contaminant is present in the original contaminated water sample.

A field test kit is also provided which includes a separatory funnel and ring stand, a pipette and pipette bulb, test tubes and a test tube rack, a graduated cylinder and the reagents.

These and other features and advantages of the present invention will be more readily understood by those skilled in the art from a reading of the following detailed description.

DETAILED DESCRIPTION OF THE PREFERRED EMBODIMENT

As previously mentioned, the present invention is based on the Friedel-Crafts alkylation of aromatic compounds promoted by Friedel-Crafts Lewis acid catalysts.

In the present method, a water sample contaminated with one or more aromatic contaminants is first extracted with an alkyl halide extractant. An especially preferred extractant is carbon tetrachloride. The extractant and water sample are introduced into an extraction apparatus such as, for example, a separatory funnel, and contacted to produce an extractant phase and a water phase. The extractant and water phases are then allowed to subsantially separate, and the extractant phase is withdrawn by draining it into a test tube or other receiving container.

At this point the extractant phase will comprise primarily the extractant and extracted aromatic contaminant The extractant phase, however, will also be saturated with water from the water phase.

To this extractant phase is added the Friedel-Crafts Lewis acid catalyst, preferably an anhydrous aluminum chloride ($AlCl_3$). Because some water will be retained within the extractant phase, it will be necessary to add an excess of catalyst because a portion of the catalyst will be used up by its reaction with the water. A large excess of catalyst is preferred to assure that sufficient catalyst will be left for the Friedel-Crafts reaction.

As a result of the Friedel-Crafts reaction, a reaction product is produced having a characteristic color indicative of the aromatic contaminant These colors and their intensity are utilized as indicators for determining both the presence, type (qualitative) and concentration (quantitative) of the aromatic contaminants.

For use in an on-site field test, the present test method requires only a minimum of equipment. Preferred components of a field test kit include a separatory funnel (1 liter) and ring stand, a pipette (5 ml) and pipette bulb, test tubes and a test tube rack, a graduated cylinder (100 ml), the reagents, i.e., the alkyl halide extractant (carbon tetrachloride) and Friedel-Crafts Lewis acid catalyst (anhydrous aluminum chloride) and containers therefor.

The following example provides a specific procedure for performing a field test for aromatic contamination in water in accordance with the present invention. This example, however, is provided as illustrative only and should not be considered limiting on the present invention.

Using a 100 ml graduated cylinder, a 100 ml water sample is poured into a 1 liter separatory funnel. About 5 ml of carbon tetrachloride is then pipetted into the separatory funnel and the contents shaken vigorously for about two minutes with periodic venting of the contents of the funnel. The separatory funnel is then place on a ring stand or like holder and the extractant and water phases are allowed to separate. The separated extractant phase (carbon tetrachloride, aromatic contaminants and any water remaining in this phase) is withdrawn by draining it into a test tube.

About 0.5 grams ($\frac{1}{4}$ teaspoon) of powdered anhydrous aluminum chloride is then added to the test tube and the contents shaken. If an aromatic contaminant is present, a characteristic color will be produced which can be observed in the remaining powder at the bottom of the test tube.

Many modifications and variations besides the embodiments specifically mentioned may be made in the techniques and structures described herein without departing substantially from the concept of the present invention. Accordingly, it should be clearly understood that the form of the invention described herein is exemplary only, and is not intended as a limitation on the scope thereof.

I claim for patent:

1. A method for on-site field testing for an aromatic contamination in a water sample, comprising the steps of:

extracting said aromatic contamination from said water sample with an alkyl halide extractant to produce an extractant phase and a water phase;

withdrawing said extractant phase from said water phase; and adding a Friedel-Crafts Lewis acid catalyst to said extractant phase to produce a reaction product having a characteristic color indicative of said aromatic contamination.

2. The method of claim 1, wherein said alkyl halide extractant comprises carbon tetrachloride.

3. The method of claim 1, wherein said Friedel-Crafts Lewis acid catalyst comprises anhdyrous aluminum chloride.

4. The method of claim 1, wherein said extracting step comprises the steps of:

introducing said alkyl halide extractant and said water sample into an extraction apparatus; and contacting said alkyl halide extractant and said water sample to produce said extractant phase and said water phase; and allowing said extractant phase and said water phase to substantially separate.

5. The method of claim 1, wherein said adding step comprises the step of adding an excess of said Friedel-Crafts Lewis acid catalyst sufficient to react with any water retained within said extractant phase.

* * * * *